United States Patent [19]

Golden et al.

[11] Patent Number: 4,890,613
[45] Date of Patent: Jan. 2, 1990

[54] TWO PIECE INTERNAL ORGAN FASTENER

[75] Inventors: Donald M. Golden, Cherry Hill, N.J.; William P. McVay, New Milford, Conn.

[73] Assignee: Ethicon, Inc., Somerville, N.J.

[21] Appl. No.: 84,665

[22] Filed: Aug. 12, 1987

Related U.S. Application Data

[63] Continuation of Ser. No. 909,348, Sep. 19, 1986, abandoned, which is a continuation of Ser. No. 736,917, May 22, 1985, abandoned, which is a continuation-in-part of Ser. No. 648,094, Sep. 7, 1984, abandoned, which is a continuation-in-part of Ser. No. 359,443, Mar. 18, 1982, abandoned.

[51] Int. Cl.$^4$ .......................... A61F 13/00; F16B 21/00
[52] U.S. Cl. ....................................... 606/220; 411/904
[58] Field of Search ............... 128/334 C, 325, 346, 128/337; 411/548, 904, 907–909, 457, 469; 227/DIG. 1

[56] References Cited

U.S. PATENT DOCUMENTS

| | | | |
|---|---|---|---|
| 3,166,072 | 1/1965 | Sullvian | 128/346 |
| 4,060,089 | 11/1977 | Noiles | 128/325 |
| 4,278,091 | 7/1981 | Borzone | 128/334 |
| 4,402,445 | 9/1983 | Green | 128/227 |
| 4,490,326 | 12/1984 | Beroff et al. | 264/328.16 |

Primary Examiner—Edward M. Coven
Assistant Examiner—Gary Jackson
Attorney, Agent, or Firm—Robert L. Minier

[57] ABSTRACT

A sterile internal organ fastening device comprising a staple and a receiver. The legs of the staple have a tapered portion terminating in a sharp point with the taper having a specific configuration to minimize penetration forces and reduce trauma and with the receiver protecting the surrounding tissue from the sharp point.

8 Claims, 2 Drawing Sheets

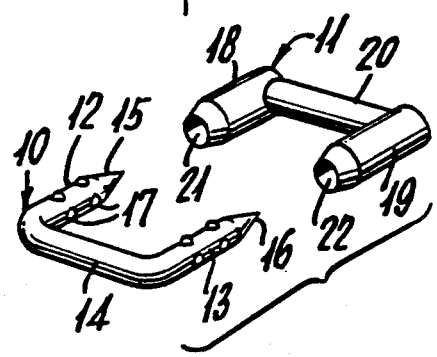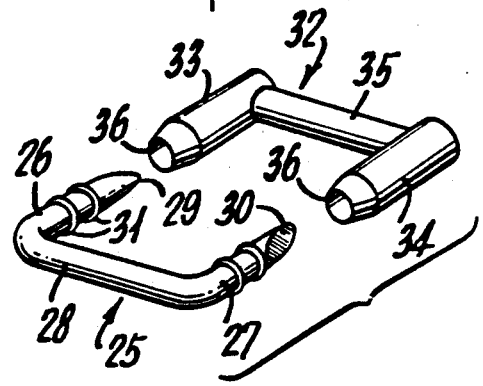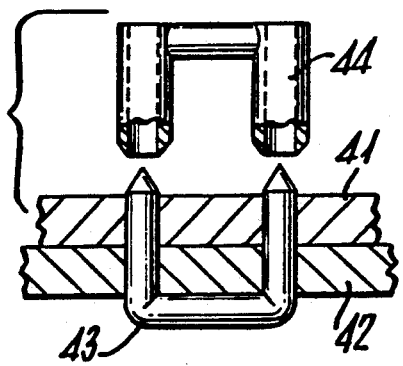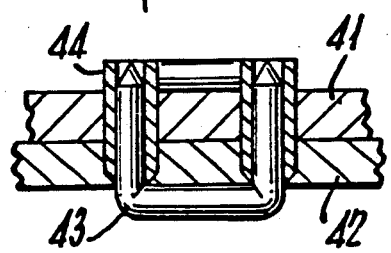

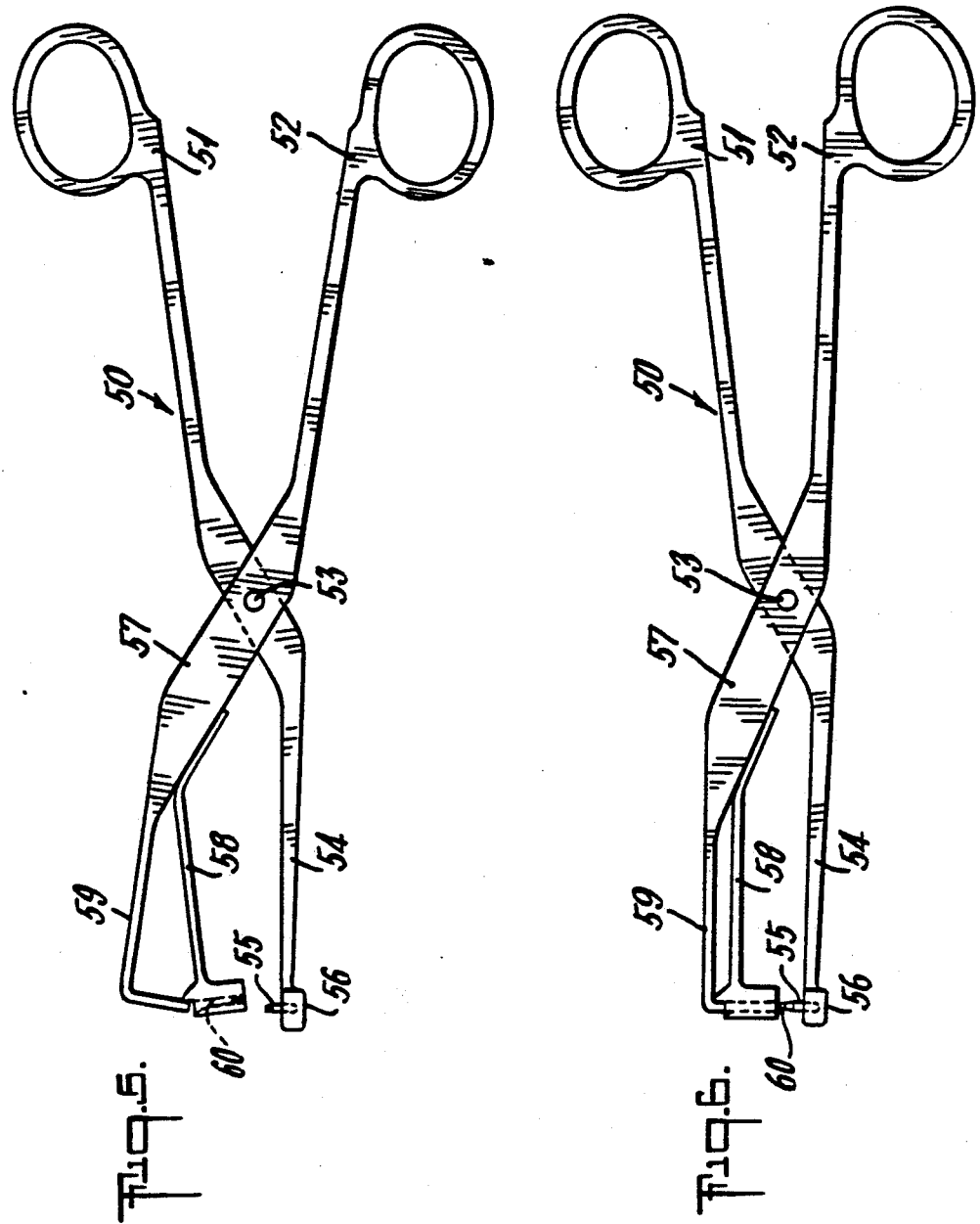

TWO PIECE INTERNAL ORGAN FASTENER

RELATED PATENT APPLICATIONS

This is a continuation of application Ser. No. 06/909,348 filed Sept. 19, 1986, now abandoned which is a continuation of Ser. No. 06/736,917 filed May 22, 1985, now abandoned which is a continuation-in-part of Ser. No. 06/648,094 filed Sept. 07, 1984, now abandoned, which is a continuation-in-part of Ser. No. 06/359,443 filed Mar. 18, 1982 now abandoned.

BACKGROUND OF THE INVENTION

The present invention relates to fasteners for internal organs and more particularly, to two-piece fasteners for connecting internal organ tissues. The fasteners are made from polymeric materials which are suitable for implantation within the body.

In various surgical procedures, it is often required to sew or repair organ walls. Generally, this is done utilizing absorable or non-absorbable sutures. Even though this is satisfactory in most instances, it is time consuming and a tedious and difficult procedure to be certain to place the suture in such a manner as to do the least amount of damage to the organ tissue while assuring a sufficient closure.

Though there have been some attempts to develop other types of closures in place of the suture for the internal organ, none have met with any substantial success as a practical manner. A critical function of the closure is tissue retention and hemostatic compression of the tissue. Also the closure should penetrate the tissue with a minimum of trauma.

We have discovered a new improved fastener for internal organs. Our improved fastener readily penetrates the organ tissues with a minimum of trauma. Our new fasteners are so constructed as not to have any rough or protruding edges when placed in the wound area. The forces to engage our new fasteners are not so great as to cause trauma and the disengagement forces are sufficient to retain the tissue in the desired position. Our new fasteners are also easier to apply and will interlock with great assurance without nemosis of the tissue.

SUMMARY OF THE PRESENT INVENTION

The sterile, internal organ, fastening mechanism for joining human or animal tissue of the present invention comprises a staple and a receiver for the staple. The staple comprises a plurality of legs with the legs connected at one end. The legs have a straight rounded portion adjacented the connection and a tapered portion extending therefrom. The tapered portion terminates in a sharp point. The length of the tapered portion measured from the start of the taper to the sharp point is at least 3 times the diameter of the straight rounded portion of the staple leg and preferably as much as 5 times the leg diameter. It is preferred that the tapered portion be conical in shape. The receiver comprises spaced apart legs. The receiver legs are connected together at one end thereof and the opposite end of the leg contains an opening for receiving the staple leg. The receiver legs enclose the sharp point to prevent the sharp point from damaging adjacent tissue and organs. The receiver legs also engage at least a portion of the straight rounded portion of the staple legs to hold the receiver and staple together during use. It is preferred that the opening be cylindrical and extend the entire length of the receiver leg. By extending the receiver leg or by depressing the portion of the receiver between the receiver legs the gap between the receiver legs and the staple legs may be reduced without undue trauma on the tissue placed between the staples and receivers. This reduced gap makes it considerably easier for the staple leg to find the appropriate opening in the reservoir when the staple leg is caused to penetrate tissue.

In certain embodiments of the present invention the staple leg and/or the inside of the receiving leg will be provided with various engagement means to make it more difficult to disengage the staple and the receiver.

The applier for the present invention is a two-jaw instrument wherein one jaw is constructed to carry the staples and the other jaw constructed to carry the receivers.

The internal organ fastener of the present invention may be formed of plastic by injection molding or other suitable technique, and may be composed of non-absorbable material, such as polypropylene, nylon and the like or absorbable material such as a homopolymer or copolymer of lactide and glycolide or polymers of p-dioxanone and the like.

DESCRIPTION OF THE DRAWINGS

FIG. 1 is an enlarged perspective view of one embodiment of a two-piece fastener in accordance with the present invention;

FIG. 2 is an enlarged perspective view of another embodiment of a two-piece fastener in accordance with the present invention;

FIG. 3 is a cross-sectional view of a two-piece fastener in accordance with the present invention with the staple member inserted in position ready to have the receiver applied;

FIG. 4 is a side elevational view of the fastener of FIG. 3 in its finished position;

FIG. 5 is a schematic view of one type of instrument for applying the two-piece fastener of the present invention, with the instrument in the open position; and FIG. 6 is a schematic view of the instrument shown in FIG. 5 in the closed position.

DESCRIPTION OF THE PREFERRED EMBODIMENT

Referring to FIG. 1, there is shown a two-piece fastener of the present invention. The fastener comprises a staple 10 and a receiving member 11 for the staple. The staple has two legs 12 and 13 connected at one end thereof by cross member 14. The free end of each leg is sharpened to a fine point 15 and 16. The sharpened tips should have a taper of at least 3 and preferably about 5 or even higher. The term 'taper' is the slope of the side starting at the body of the leg and extending to the point. A taper of 3 would mean that the vertical distance of the leg measured from where the taper begins to the point of the tip is 3 times the diameter of the leg. The higher the taper number, the lower the penetration force and the less the trauma caused to the tissue when placing the staple. The taper is preferably a conical taper. The surfaces of the legs of the staples contain raised bosses 17 to provide for a more permanent fit with the receiver. The receiver comprises a pair of spaced apart legs 18 and 19 adapted to accept the legs of the staple. The receiver legs are connected at one end by cross member 20 and the legs have openings 21 and 22 extending the full length of the leg. The openings are round and each opening is just slightly greater than the diameter of a leg of the staple. We have discovered that tolerances of from about 0.002 to 0.004 inch between the staple leg and the receiver opening are satisfactory. Preferably the ends of the receiver leg openings are sharpened to assist in penetration of the receiver legs through tissue. The raised bosses on the staple legs engage the inner surface of the receiver when the staple is inserted in the receiver. It is preferred that the ends of the legs of the receiver by sharpened to aid in the insertion of the receiver through the tissue and reduce trauma caused by the insertion of the fastening device.

Referring to FIG. 2 there is shown another embodiment of the fastener of the present invention. The staple 25 comprises a pair of legs 26 and 27 connected at one end by a crosspiece 28. The legs are bias cut to a sharp point 29 and 30. Disposed on the surface of each leg are a series of raised areas 31 extending around the circumference of the leg. The receiver 32 comprises a pair of legs 33 and 34 connected by crosspiece 35. Each leg has an opening 36 extending the length of the leg for accepting the leg of the staple.

In the embodiments depicted in FIGS. 1 and 2 the length of the legs of the receiver is substantially the same as the length of the legs of the staple. The legs themselves are connected at their opposite end by a cross member. By maintaining these lengths equivalent the pointed ends of the staple are protected while in use so they cannot harm the wound area. Also by connecting the legs only at the opposite ends thereof the amount of material used in each staple is kept to a minimum, and the size of each fastener is reduced. Hence, more staples may be implanted at a time.

Also by extending the receiver legs the gap or distance between the tip of the staple leg and the tip of the receiver leg, prior to application of the fastener, may be reduced. The staple may be placed on one side of the tissue to be joined and the receiver on the opposite side of the tissue to be joined. The two parts may be moved together to compress the tissue and force a portion of the tissue between the receiver legs thus reducing the amount of tissue and the distance between the tip of the staple leg and the tip of the receiver leg. This results in shortening the distance the staple leg has to pass through tissue before the staple leg engages the receiver leg which greatly improves the reliability with which the fasteners are joined. The structure of the novel fasteners of the present invention unexpectedly has greater reliability in interlocking between the staple and fastener when joining tissue and cause very little trauma to the joined tissue.

Referring to FIGS. 3 and 4, there is shown a fastening device of the present invention as it is being inserted between layers of tissue 41 and 42. The staple 43 has its legs first inserted through the appropriate layers of the organ member. It is positioned as shown in the drawing with its legs just extending to the upper portion of the tissue layer. As shown in FIG. 4, the receiving member 44 is disposed about the legs of the staple in its final position.

The fastening members of the present invention have an improved penetration force; i.e., the force required to penetrate any given piece of tissue with the staple of our new fastener is greatly reduced. Hence, the resulting trauma occurring from the closure procedure is reduced.

The penetration test is a force measurement which measures the force in grams required to pierce, cut or pass through a membrane. In our tests the membrane used is a 2 mil thick Mylar film. The test is performed at a constant velocity and the data reported is the greatest force measured during the penetration of the membrane. An Instron TTDL Testing Machine is used. A suitable piece of membrane is placed in the Testing Machine. A staple leg to be tested is placed in a jaw of the Instron Testing Machine. The jaw holding the staple leg is urged toward the membrane and through the membrane at a constant speed of 5 inches per minute. The force in grams required to penetrate the membrane is measured. A leg is tested 5 times and the average results reported.

The tip configurations tested are the cone tip depicted in FIG. 1 and the sharpened bias tip depicted in FIG. 2. Various taper ratios are tested; that is, the ratio of tip length (L) to diameter (D). The results of these tests are given in Table 1.

TABLE I

| L/D | Shape Tip | Penetration Force (Grams) Mean Standard | Deviation |
|---|---|---|---|
| 1.0 | Cone | 132.7 | 7.4 |
| 1.0 | Sharpened Bias | 139.3 | 10.4 |
| 3.0 | Cone | 85.0 | 3.1 |
| 3.0 | Sharpened Bias | 71.7 | 8.3 |
| 5.0 | Cone | 74.6 | 11.0 |
| 5.0 | Sharpened Bias | 56.0 | 7.6 |

As may be seen from the above table at L/D ratio or tapers of 3 or more the force to penetrate the film is greatly reduced.

Two other properties which are extremely important for internal organ fasteners are the force required to engage the two members and the force required to disengage the two members. The greater the force required to engage the two members the greater the probability of causing trauma to the wound area and also the greater the trauma that may be caused. The greater the force to disengage the two members the less chance the fastener will come apart once implanted and the more of the disengagement force that will remain when the fastener is made from an absorbable polymer and is slowly being absorbed. As previously mentioned the new fasteners of the present invention have low engagement forces yet good disengagement forces so that once engaged they will stay engaged during use.

The engagement force is measured using an Instron TTDL Testing Machine.

The engagement force is determined by placing the receiver and staple in the jaws of a single shot tacking instrument of an Instron TTDL Testing Machine. The pusher jaw is clamped in the Instron and the lower half placed on a compression load cell. The Instron is set so that a 1.0 mm gap is obtained after the staple is pushed into the receiver. The crosshead is brought up at a constant speed of 2 inches/min. until the predetermined gap is reached. At this point the test is stopped and the maximum load recorded. The test parameter to be used for the engagement test are:

| Crosshead speed | 2.0 inches/minute |
| Chart speed | 5.0 inches/minute |
| Full Scale Load | 20 pounds |

The disengagement force is measured using an Instron TDDL Testing Machine.

The disengagement test is run by placing the receiver in a pair of forceps which are clamped in a jaw attached to the crosshead of an Instron TTDL Testing Machine. A strip of stainless steel foil is cut and placed between the staple and receiver and then clamped in a jaw attached to the load cell of the Instron. The staple is pulled straight up until complete separation is achieved. The test parameters to be used for the disengagement tests are:

| Crosshead speed | 0.1 inches/minute |
| Chart speed | 5.0 inches/minute |
| Full Scale Load | 5 pounds; 10 pounds |

In this test 10 samples are run and the average forces are calculated.

TABLE II

| Fastener Description | Mean Engagement | | Mean Disengagement | |
| --- | --- | --- | --- | --- |
| | Force Deviation | Standard (lbs.) | Force Deviation | Standard (lbs.) |
| Staple and Receiver Similar to FIG. 2 made from polydioxanone | 7.09 | .64 | 3.08 | .36 |
| Staple and Receiver Similar to FIG. 1 made from polydioxanone | 7.16 | 1.28 | 3.02 | .44 |

Devices of the present invention may be constructed in various sizes according to their intended function. Fastening devices are typically less than ⅜ inch in the space from leg to leg and usually less than ¼ inch in the height of the legs. The various sizes of such fastening devices are matched with individual applying instruments having their jaws tailored to the size of the fastening a device for best performance.

One type of instrument that may be used to apply the fasteners of the present invention is shown in FIGS. 5 and 6.

A scissors type instrument 50 is shown. The instrument comprises a pair of forceps type handles 51 and 52 which are pivotally connected at 53. The forward end 54 of one handle frictionally grasps and holds the receiver portion of the fastener in a cavity or opening 56. The forward end 57 of the opposite handle is sectioned into a bottom or lower holding member 58 and a top or upper inserting member 59. The holding member frictionally holds the staple portion 60 of the fastener. In operation a receiver is placed in cavity 56 and a staple placed in holding member 58. The tissue to be closed is placed between the receiver and staple and the scissors or forceps handles urged toward one another. This motion urges the holding member downwardly toward the cavity holding the receiver. The continued urging together of the forceps handles causes the inserting member to be brought downwardly pushing the staple out of the holding member into the receiver tying the tissue between the staple and receiver. Releasing the forceps handle opens the gap between the holding member and cavity and allows for the frictional disengagement of the fastener from the instrument.

The fastening devices of the present invention are most conveniently molded of biologically acceptable plastic materials which may be absorbable or non-absorbable. Preferred absorbable polymers include homopolymers and copolymers of glycolide and lactide and p-dioxanone. Preferred non-absorbable polymers include nylon, polyester and polypropylene. All these materials have been demonstrated to be biologically acceptable when used as sutures or other implantable medical devices. In certain instances, it may be desirable to make the staple from one polymer component and the receiver from a different polymer component. We found it especially suitable to make a staple from an absorbable polymer of glycolide and lactide to provide a rigid staple with very sharp pointed tips while making the receiver from a homopolymer of dioxanone to provide a strong receiver with minimal distortion. The fasteners of the present invention are made from solid polymer materials by the various molding techniques such as injection molding.

The fastening devices of the present invention are sterilized prior to use. Depending on the material used to make the fastening device the device may be sterilized by any of the well-known sterilizing techniques: such as; irradiation, gas treatment (i.e., ethylene oxide), heat treatment and the like. The sterile device is packaged in a sterile package as is well-known in the art.

Having thus described the present invention and various embodiments thereof it will be readily apparent to one skilled in the art that various modifications and alterations may be made thereto without departing from the spirit and scope of the present invention.

What is claimed:

1. A sterile internal organ fastening device, for joining human or animal tissue, said device comprising a staple having improved penetration characteristics and a receiver for said staple, said staple having a pair of substantially round, spaced apart legs connected together at one end of the staple, each of said legs having a straight rounded portion adjacent said connected area and a tapered portion extending from said straight portion, said tapered portion terminating in a sharp point, the length of the tapered portion, measured from the start of the taper to the sharp point, being at least three times the diameter of the straight rounded portion whereby said staple leg has improved penetration characteristics, said receiver having a pair of spaced apart legs connected together at one end of the receiver, the free end of each of said receiver legs having a substantially round opening therein for accepting the leg of said staple, said opening adapted to engage said staple leg to hold said staple and receiver together.

2. An internal organ fastening device in accordance with claim 1, wherein the tapered portion of each leg of the staple is conically shaped.

3. An internal organ fastening device in accordance with claim 1 or 2, wherein the length of the tapered portion, measured from the start of the taper to the sharp point, is at least five times the diameter of the straight rounded portion of the staple leg.

4. A sterile internal organ fastening device for joining human or animal tissue comprising a staple to be placed on one side of the tissue to be joined and a receiver to be placed on the opposite side of the tissue to be joined, said staple comprising a pair of spaced apart legs, said staple legs being connected together at one end of each leg, the opposite end of each staple leg being free and terminating in a sharp point, said receiver having a pair of spaced apart legs, said legs being connected together at one end of each leg, the opposite end of each receiver leg being free to produce an open area bounded by the receiver and opening in the free end of each receiver leg for accepting and interlocking with a staple leg, whereby when the staple is placed on one side of the tissue to be joined with the free ends of the staple legs directed towards said tissue and the receiver is placed on the opposite side of the tissue to be joined with the free ends of the staple legs directed towards said tissue and the receiver is placed on the opposite side of the tissue to be joined with the free ends of the receiver legs directed towards said tissue the distance between the free ends of the staple legs and the free ends of the receiver legs may be reduced and excess tissue allowed to enter the open area between the receiver legs to reduce the amount of tissue the free ends of the staple legs have to penetrate before engaging the openings in the free ends of the receiver legs and interlocking therewith to hold said staple and receiver together.

5. A sterile internal organ fastening device in accordance with claim 4 wherein the opening extends the entire length of the free end of a receiver leg.

6. A sterile internal organ fastening device in accordance with claim 4 or 5 wherein the length of the receiver legs is substantially the same as the length of the staple legs.

7. An internal organ fastening device in accordance with claim 4, made from an absorbable polymeric material.

8. An internal organ fastening device in accordance with claim 4 or 7, wherein the staple is made from a copolymer of glycolide and lactide and the receiver is made from a homopolymer of dioxanone.

* * * * *

UNITED STATES PATENT AND TRADEMARK OFFICE
CERTIFICATE OF CORRECTION

PATENT NO. : 4,890,613

DATED : January 2, 1990

INVENTOR(S) : Donald M. Golden et al.

It is certified that error appears in the above-identified patent and that said Letters Patent is hereby corrected as shown below:

Claim 4, column 6, line 66, after "receiver" please change "and" to "an".

Claim 4, column 7, lines 2-5, after "said tissue and", please delete "the receiver is placed on the opposite side of the tissue to be joined with the free ends of the staple legs directed towards said tissue and".

Signed and Sealed this

Eighteenth Day of December, 1990

Attest:

HARRY F. MANBECK, JR.

Attesting Officer

Commissioner of Patents and Trademarks